US010739285B2

(12) United States Patent
Dohi et al.

(10) Patent No.: US 10,739,285 B2
(45) Date of Patent: Aug. 11, 2020

(54) EVALUATING METHOD FOR COAL AND PRODUCING METHOD FOR COKE (71) Applicant: JFE STEEL CORPORATION, Tokyo (JP)

(72) Inventors: Yusuke Dohi, Fukuyama (JP); Kiyoshi Fukada, Fukuyama (JP); Takashi Matsui, Fukuyama (JP); Mikiya Nagayama, Fukuyama (JP); Narumi Nanri, Fukuyama (JP); Kazutoshi Hanada, Chiba (JP)

(73) Assignee: JFE STEEL CORPORATION, Tokyo (JP)

( * ) Notice: Subject to any disclaimer, the term of this patent is extended or adjusted under 35 U.S.C. 154(b) by 0 days.

(21) Appl. No.: 15/553,049

(22) PCT Filed: Feb. 17, 2016

(86) PCT No.: PCT/JP2016/000808
§ 371 (c)(1),
(2) Date: Aug. 23, 2017

(87) PCT Pub. No.: WO2016/136191
PCT Pub. Date: Sep. 1, 2016

(65) Prior Publication Data
US 2018/0031501 A1  Feb. 1, 2018

(30) Foreign Application Priority Data

Feb. 25, 2015  (JP) .................. 2015-034990

(51) Int. Cl.
C10B 53/00  (2006.01)
C10B 57/04  (2006.01)
(Continued)

(52) U.S. Cl.
CPC ............. *G01N 25/04* (2013.01); *C10B 45/00* (2013.01); *C10B 53/04* (2013.01); *C10B 57/06* (2013.01);
(Continued)

(58) Field of Classification Search
CPC ......... C10B 57/00; C10B 57/04; C10B 57/06; C10B 57/08; C10B 53/00
See application file for complete search history.

(56) References Cited

U.S. PATENT DOCUMENTS 6,830,660 B1 * 12/2004 Yamauchi ............... C10B 57/04
201/21
9,340,740 B2  5/2016 Dohi et al.
2014/0144071 A1  5/2014 Dohi et al.

FOREIGN PATENT DOCUMENTS

CN    1286722 A    3/2001
CN    103189474 A   7/2013
(Continued)

OTHER PUBLICATIONS

Human translation of Kojima (JP S60-144386 A) obtained from the USPTO.*
(Continued)

*Primary Examiner* — Jonathan Luke Pilcher
(74) *Attorney, Agent, or Firm* — Ratnerprestia (57) ABSTRACT A method for accurately measuring the thermoplasticity of a coal whose thermoplasticity has been difficult to evaluate and determining whether the coal that is to be measured does not significantly reduce the coke strength when used for a coal blend is disclosed. Also disclosed is a method for evaluating a coal used as a raw material for coke and includes using a physical property value relating to a thermoplasticity of a coal as an index for evaluating the coal, wherein a primary or secondary amine including an aromatic
(Continued)

ring have been added to the coal, thereby enhancing the thermoplasticity of the coal.

8 Claims, 5 Drawing Sheets

(51) Int. Cl.
    *G01N 25/04* (2006.01)
    *C10B 57/06* (2006.01)
    *C10B 45/00* (2006.01)
    *C10B 53/04* (2006.01)
    *C10L 10/00* (2006.01)
    *G01N 33/22* (2006.01)

(52) U.S. Cl.
    CPC ............ *C10L 10/00* (2013.01); *G01N 33/222* (2013.01); *C10B 53/00* (2013.01); *C10B 57/04* (2013.01); *C10L 2200/0259* (2013.01)

(56) References Cited

FOREIGN PATENT DOCUMENTS

| CN | 102559227 | B  | 3/2014  |
|----|-----------|----|---------|
| EP | 1026223   | A1 | 8/2000  |
| JP | 60144386  | A  | 7/1985  |
| JP | 61285286  | A  | 12/1986 |
| JP | 62285051  | A  | 12/1987 |
| JP | 039991    | A  | 1/1991  |
| JP | 2000073070| A  | 3/2000  |
| JP | 2009249596| A  | 10/2009 |
| JP | 2014043545| A  | 3/2014  |
| JP | 2015040270| A  | 3/2015  |
| RU | 2013114317| A  | 10/2014 |
| TW | 201217768 | A  | 5/2012  |

OTHER PUBLICATIONS

ChemicalBook.com, "N,N'-di-2-naphthyl-phenylenediamine", Sep. 15, 2013 (date obtained from Wayback Machine), Available online at: https://web.archive.org/web/20130915072619/https://www.chemicalbook.com/ChemicalProductProperty_En_CB4242789.htm (Year : 2013).*

Russian Office Action for Russian Application No. 2017129805/05, dated Jun. 1, 2018, with Concise Statement of Search Report, 9 pages.

Korean Office Action for Korean Application No. 10-2017-7022813, dated Jun. 11, 2018, with Concise Statement of Relevance of Office Action, 7 pages.

International Search Report and Written Opinion for International Application No. PCT/JP2016/000808, dated Apr. 12, 2016—6 Pages.

Taiwanese Office Action for Taiwanese Application No. 105105461, dated Dec. 12, 2016, including Concise Statement of Search Report, 8 pages.

Extended European Search Report for European Application No. 16 754 943.5, dated Jan. 25, 2018, 8 pages.

Communication Pursuant to Article 94(3) for European Application No. 16 754 943.5, dated Mar. 4, 2019, 5 pages.

Chinese Office Action for Chinese Application No. 201680011656.0, dated Aug. 26, 2019 with Concise Statement of Relevance of Office Action, 8 pages.

First Chinese Search Report for Chinese Application No. 201680011656.0, dated Aug. 16, 2019, 1 page.

Japanese Office Action for Japanese Application No. 2017-050781, dated Dec. 10, 2019 with Concise Statement of Relevance of Office Action, 3 pages.

Chinese Office Action for Chinese Application No. 201680011656.0, dated Mar. 30, 2020, with Concise Statement of Relevance of Office Action, 7 pages.

* cited by examiner

EVALUATING METHOD FOR COAL AND PRODUCING METHOD FOR COKE

CROSS REFERENCE TO RELATED APPLICATIONS

This application is the U.S. National Phase Application of PCT International Application No. PCT/JP2016/000808, filed Feb. 17, 2016, and claims priority to Japanese Patent Application No. 2015-034990, filed Feb. 25, 2015, the disclosures of both applications being incorporated herein by reference in their entireties for all purposes.

FIELD OF THE INVENTION

The present invention relates to an evaluating method for a coal used as a raw material for coke and a producing method for a coke by the carbonization of a coal blend including a coal evaluated by the evaluating method.

BACKGROUND OF THE INVENTION

Since coke used in a blast furnace is required to have a high strength, it is desirable to use a coal having a high caking property as a raw material for coke. However, all of mined coals do not have a high caking property; some of the mined coals may have a low caking property. Therefore, in common, plural types (brands) of coals having different properties are mixed together to form a coal blend, which is used as a raw material for coke. The caking property of a coal is an essential property for producing coke, which causes the coal to be melted and solidified in the carbonization of the coal. The caking property of a coal is determined on the basis of the properties of the coal when the coal is melted. Therefore, whether or not a brand of coal is suitable as a raw material for coke may be readily determined by effectively using a value on thermoplastic property (measured value or estimated value) of the coal as a measure.

In many cases, the higher the caking property of a coal, the higher the price of the coal; the lower the caking property of a coal, the lower the price of the coal. Thus, using a "non- or slightly caking coal" as a raw material for coke in a larger amount advantageously limits the costs of raw materials. However, it is not easy to evaluate the usability of a non- or slightly caking coal as a raw material for coke, because it is difficult (or, not possible) to measure a value on a thermoplastic property of a non- or slightly caking coal having a low (or, negligible) caking property by a method for testing the fluidity of coal by a Gieseler plastometer method defined in JIS M 8801, or a method for evaluating the caking property of a caking coal such as dilatometer method.

For the above context, a method for measuring (evaluating) the thermoplasticity of a non- or slightly caking coal has been developed. For example, it is described in Patent Literature 1 and Patent Literature 2 that the fluidity of a coal is measured by a Gieseler plastometer method under the conditions where the rate of temperature rise is set to 5° C./min or more, which is higher than the rate of temperature rise (3° C./min) specified in JIS M 8801, since the fluidity of a coal increases with an increase in the rate of temperature rise. In particular, it is described in Patent Literature 2 that the usability of a non- or slightly caking coal as a raw material for coke may be readily determined by the method proposed in Patent Literature 2, because there is a good correlation between the maximum fluidity (MF) of the non- or slightly caking coal which is measured with an increased rate of temperature rise and the CSR (coke strength after $CO_2$ reaction) of a coke produced by the carbonization of a coal blend prepared by blending the non- or slightly caking coals.

In the method described in Patent Literature 3, the estimated fluidity of a noncaking coal is determined as a value on thermoplastic property of the noncaking coal. It is described in Patent Literature 3 that, in the above method, the fluidity A of a caking coal and the fluidity B of a coal blend that includes a noncaking coal and the caking coal are measured, and the estimated fluidity D that makes the fluidity B when added to the fluidity A is considered to be a value on thermoplastic property of the noncaking coal.

PATENT LITERATURE

PTL 1: Japanese Unexamined Patent Application Publication No. 62-285051
PTL 2: Japanese Unexamined Patent Application Publication No. 2000-73070
PTL 3: Japanese Unexamined Patent Application Publication No. 3-9991
PTL 4: Japanese Unexamined Patent Application Publication No. 2014-43545

SUMMARY OF THE INVENTION

Although the methods described in Patent Literature 1 and Patent Literature 2, in which the fluidity of a coal is measured by a Gieseler plastometer method with an increased rate of temperature rise, are simple and easy, questions remain as to a correspondence between the fluidity and the coke strength; in Patent Literature 1, no mention is made of the relationship between the fluidity of a coal which is measured by a Gieseler plastometer method with an increased rate of temperature rise and the coke strength. It is described in Patent Literature 2 that there is a good correlation between the MF of a non- or slightly caking coal which is measured with an increased rate of temperature rise and the CSR (coke strength after $CO_2$ reaction) of a coke produced by the carbonization of a coal blend prepared by mixing the non- or slightly caking coal with a coal other than non- or slightly caking coal (hereinafter, referred to as "balance coal"). However, the non- or slightly caking coals described in Examples of Patent Literature 2 are bituminous coals having a degree of coalification (mean maximum reflectance of vitrinite Ro) of 0.96 to 1.16, which are considerably limited examples. It is not clear whether the good correlation between the MF of a non- or slightly caking coal and the coke strength holds also in the case where a non- or slightly caking coal other than bituminous coal is used.

Even when the estimated fluidity of a non- or slightly caking coal is determined by the method described in Patent Literature 3, a non- or slightly caking coal having a high estimated fluidity is evaluated as being usable as a raw material for coke, and the non- or slightly caking coal is included in a coal blend, the relationship between the strength of a coke produced by the carbonization of the coal blend and the estimated fluidity of the non- or slightly caking coal is not clear and, therefore, the validity of using the estimated fluidity of the non- or slightly caking coal for determining whether the non- or slightly caking coal does not significantly reduce the coke strength and is usable as a raw material for coke is not clear. The method for determining the estimated fluidity of a noncaking coal which is described in Patent Literature 3 may not be valid for the above evaluation because it is known that the fluidity of a coal blend may be affected by the interaction between coals and the estimated fluidity of a noncaking coal may vary with the brand of a caking coal used in combination with the noncaking coal.

Patent Literature 4 discloses a fact that adding a primary or secondary amine including an aromatic ring to a coal used as a raw material for coke may enhance the fluidity of the coal. However, Patent Literature 4 does not relate to a technique for evaluating the thermoplasticity of a non- or slightly caking coal.

The present invention was made in light of the above-described issues. It is an object of the present invention to provide a method for accurately measuring the thermoplasticity of a coal (in particular, non- or slightly caking coal) whose thermoplasticity has been difficult to evaluate and determining whether the coal that is to be measured does not significantly reduce the coke strength when used for a coal blend.

The summary of embodiments of the present invention that may address the above-described issues is as follows.

(1) An evaluating method for a coal used as a raw material for coke, the method using including: using a physical property value relating to a thermoplasticity of a coal as an index for evaluating the coal, wherein a primary or secondary amine including an aromatic ring have been added to the coal, thereby enhancing the thermoplasticity of the coal.

(2) The evaluating method according to (1), wherein the coal has a Gieseler maximum fluidity MF of 20 ddpm or less before the amine is added to the coal.

(3) The evaluating method according to (1) or (2), wherein the amine is N,N'-di-2-naphthyl-p-phenylenediamine.

(4) The evaluating method according to any one of (1) to (3), wherein the physical property values of each coal of plural brands of coals have already been measured; and a plurality of coke strength have already been measured, each of the plurality being measured for a coke produced by carbonization of a coal blend including the each coal of which the physical property value has already been measured; the method further comprising: determining a physical property value corresponding to a target value of coke strength from a relational formula between the measured physical property values and the plurality of the coke strength corresponding to each of the measured physical property values; and evaluating a coal of which a physical property value from measurement is equal to or larger than the determined physical property value as being usable for a raw material for coke.

(5) A producing method for a coke using the evaluating method according to (4), the producing method comprising:

carbonizing a coal blend including the coal evaluated as being usable, to produce a coke.

According to embodiments the present invention, it is possible to determine a coal (in particular, a non- or slightly caking coal) for a coal blend capable of maintaining the coke strength at a high level.

DESCRIPTION OF EMBODIMENTS

The difficulty in measuring the thermoplasticity of a non- or slightly caking coal and determining whether the non- or slightly caking coal is capable of maintaining the coke strength at a high level in the related art is described below.

Four types of coals (Coals A to D) were prepared as examples of non- or slightly caking coals that are to be evaluated. The mean maximum reflectance of vitrinite Ro, the volatile matter content VM, and the Gieseler maximum fluidity MF of each of Coals A to D were measured. For measuring mean maximum reflectance of vitrinite Ro, the method defined in JIS M 8816 was used. For measuring volatile matter content VM, the method defined in JIS M 8812 was used. For measuring Gieseler maximum fluidity MF, the method defined in JIS M 8801 was used. Table 1 shows the Ro [%], VM [%, dry basis], and MF [ddpm] of each of Coals A to D. As shown by Gieseler maximum fluidity MF in Table 1, Coals A, B, and D are noncaking coals, and Coal C is a slightly caking coal.

TABLE 1

| Item<br>Unit | Ro<br>% | VM<br>% dry basis | MF<br>ddpm |
|---|---|---|---|
| Coal A (semianthracite) | 1.61 | 18.0 | 0 |
| Coal B (subbituminous coal) | 0.53 | 32.5 | 0 |
| Coal C (subbituminous coal) | 0.52 | 32.0 | 5 |
| Coal D (anthracite) | 2.06 | 13.5 | 0 |

The impact of each of the non- or slightly caking coals (Coals A to D) on the coke strength which may occur when the non- or slightly caking coal is included in a coal blend was determined using a carbonization test oven. The blending ratios of the non- or slightly caking coals in the respective coal blends were set to 20% by mass. The balance coal used was a coal prepared by mixing plural brands of coals such that the weighted mean Ro of the coal which was weighted by the blending ratios of the coals was 1.03 and the mean of the common logarithms of MF (log MF) (mean weighted by the blending ratios of the coals) was 2.3. Coals A to D were each mixed with the balance coal to form four types of coal blends.

The coal blends were each charged into a carbonization vessel such that the bulk density (based on dry weight) of the coal blend was 930 kg/m$^3$. While the bulk density of a coal charged is about 700 to 800 kg/m$^3$ in the operation of a common coke oven in which a coal is charged from the upper part of the coke oven chamber, the carbonization test described herein was conducted under the conditions where the bulk density was relatively high in order to emphasize the differences among the coal blends. Since coals having poor qualities such as non- or slightly caking coals are used and the bulk density of a coal charged in the coke oven is increased by a mechanical operation (e.g., stamp charging) in order to maintain the coke strength after carbonization even in the operation of a commercial coke oven, the above test conditions where the bulk density (based on the dry weight) of each coal blend is set to 930 kg/m$^3$ are preferable in order to estimate the results that may be obtained when carbonization is performed at a high bulk density.

Carbonization of a coal was performed for 6 hours in an electric furnace having a furnace temperature of 1050° C. with a 10-kg weight being placed on the carbonization vessel. Subsequently, the carbonized coal was removed from the electric furnace and cooled with nitrogen. Hereby, coke was prepared. In accordance with the method for testing drum strength described in JIS K 2151, the coke was each rotated 150 times at a rotational speed of 15 rpm, and the mass proportion of coke particles having a diameter of 15 mm or more was measured. The drum strength index DI(150/15) [-] calculated by multiplying the mass ratio relative to the coke that has not been rotated by 100 was used for evaluating the coke strength. The balance coal was also carbonized alone as in the carbonization of the coal blends to form a coke. The drum strength DI(150/15) [-] of the coke was determined.

The usability of each of the non- or slightly caking coals as a raw material for coke was evaluated on the basis of the difference ΔDI calculated by subtracting the drum strength of a coke prepared from only the balance coal from the drum strength of a coke prepared from a coal blend including the corresponding one of Coals A to D. A negative ΔDI indicates that the addition of the non- or slightly caking coal reduced the coke strength compared with the coke prepared from only the balance coal.

Figure 1:
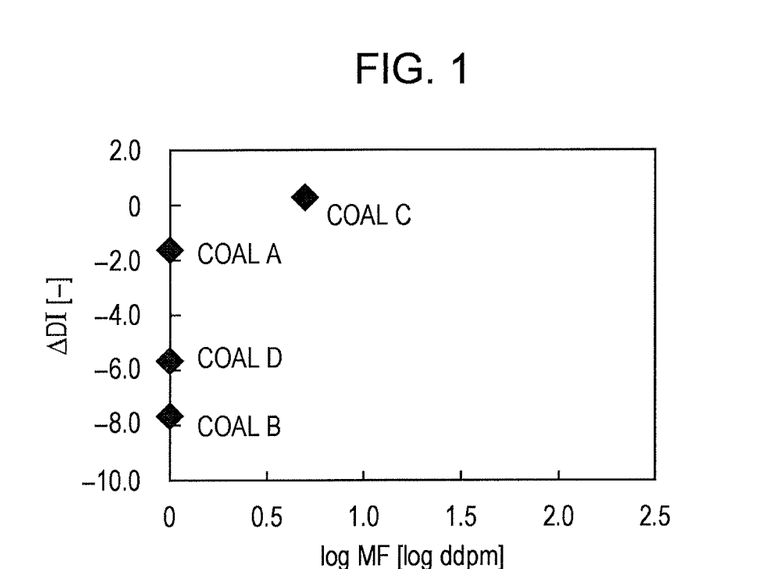
FIG. 1 is a graph illustrating the relationship between the common logarithm values (log MF [log ddpm]) of the Gieseler maximum fluidity MF of the evaluated coals and the differences $\Delta DI$ (DI (150/50)[−]) each calculated by subtracting the drum strength of a coke prepared from a coal blend including a corresponding one of the evaluated coals from the drum strength of a coke prepared from a balance coal that is a portion of the coal blend excluding the evaluated coal.

FIG. 1 illustrates the relationship between the log MF values of Coals A to D and ΔDI values. Although the MF values of Coals A, B, and D are 0 (zero) ddpm, the log MF values of Coals A, B, and D are denoted as "0" for convenience in the graph of FIG. 1.

The graph illustrated in FIG. 1 confirms that the strength of a coke prepared from a coal blend including at least Coal A, B, or D was smaller than that of a coke prepared from only the balance coal. It is also confirmed that, although the log MF values of the non- or slightly caking coals (Coals A to D) do not vary greatly, the amounts of reductions (ΔDI of FIG. 1) in the plurality of strength of coke prepared from the coal blends compared with the strength of a coke prepared from only the balance coal, which did not include the non- or slightly caking coal, varied with the types of the non- or slightly caking coals included in the coal blends. This proves the difficulty in determining the impact of the type of non- or slightly caking coal on the coke strength only by measuring the physical property value (Gieseler maximum fluidity MF) of the non- or slightly caking coal which relates to thermoplasticity.

The method described in Patent Literature 1 and Patent Literature 2 that are the related art, in which MF is measured with an increased rate of temperature rise was tested. In a Gieseler plastometer method, a retort in which a coal sample is placed is immersed in a soldering bath maintained at 300° C. and heated at 3° C./min. The inventors of the present invention immersed a retort including a coal sample placed therein was immersed in a soldering bath maintained at 550° C. in order to increase the rate of temperature rise and measured the fluidity of the coal sample. The measurement of the temperature inside the sample heated under the above conditions confirmed that the rate of temperature rise was about 75° C./min.

Figure 2:
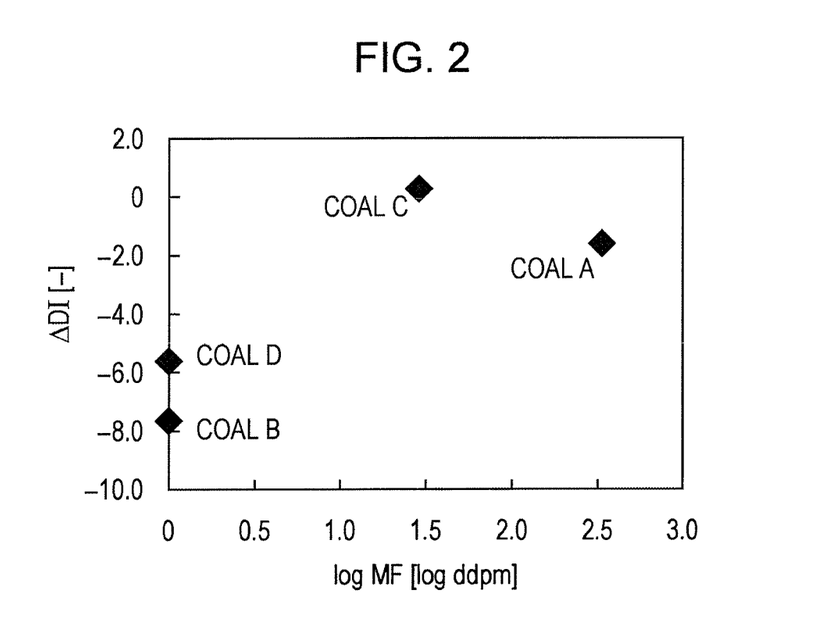
FIG. 2 is a graph illustrating the relationship between the log MF values of coals which were measured with an increased rate of temperature rise and the $\Delta DI$ values.

Table 2 shows the measurement results. FIG. 2 illustrates the relationship between log MF and coke strength. The graph illustrated in FIG. 2 confirms the variation in fluidity among the brands of coal. However, ΔDI did not increase with an increase in log MF. That is, a good positive correlation between log MF and ΔDI was not confirmed.

TABLE 2

| Item | MF | MF with high rate of temperature rise |
|---|---|---|
| Unit | | ddpm |
| Coal A (semianthracite) | 0 | 336 |
| Coal B (subbituminous coal) | 0 | 0 |
| Coal C (subbituminous coal) | 5 | 29 |
| Coal D (anthracite) | 0 | 1 |

Whether the impact of a non- or slightly caking coal on the coke strength can be evaluated on the basis of the estimated fluidity (Gieseler maximum fluidity) of the non- or slightly caking coal by applying the contents of Patent Literature 3 that is the related art was determined. A caking coal was added to each of the non- or slightly caking coals that were to be evaluated to prepare coal blends, and the MF values of the resulting coal blends were evaluated. Coals E and F were prepared as caking coals, which served as a balance coal that is a portion of a coal blend excluding Coals A to D. Table 3 shows the Ro, VM, and MF values of Coals E and F.

TABLE 3

| Item | Ro | VM | MF |
|---|---|---|---|
| Unit | % | % dry basis | ddpm |
| Coal E | 0.70 | 39.6 | 970 |
| Coal F | 0.98 | 27.0 | 415 |

Figure 3:
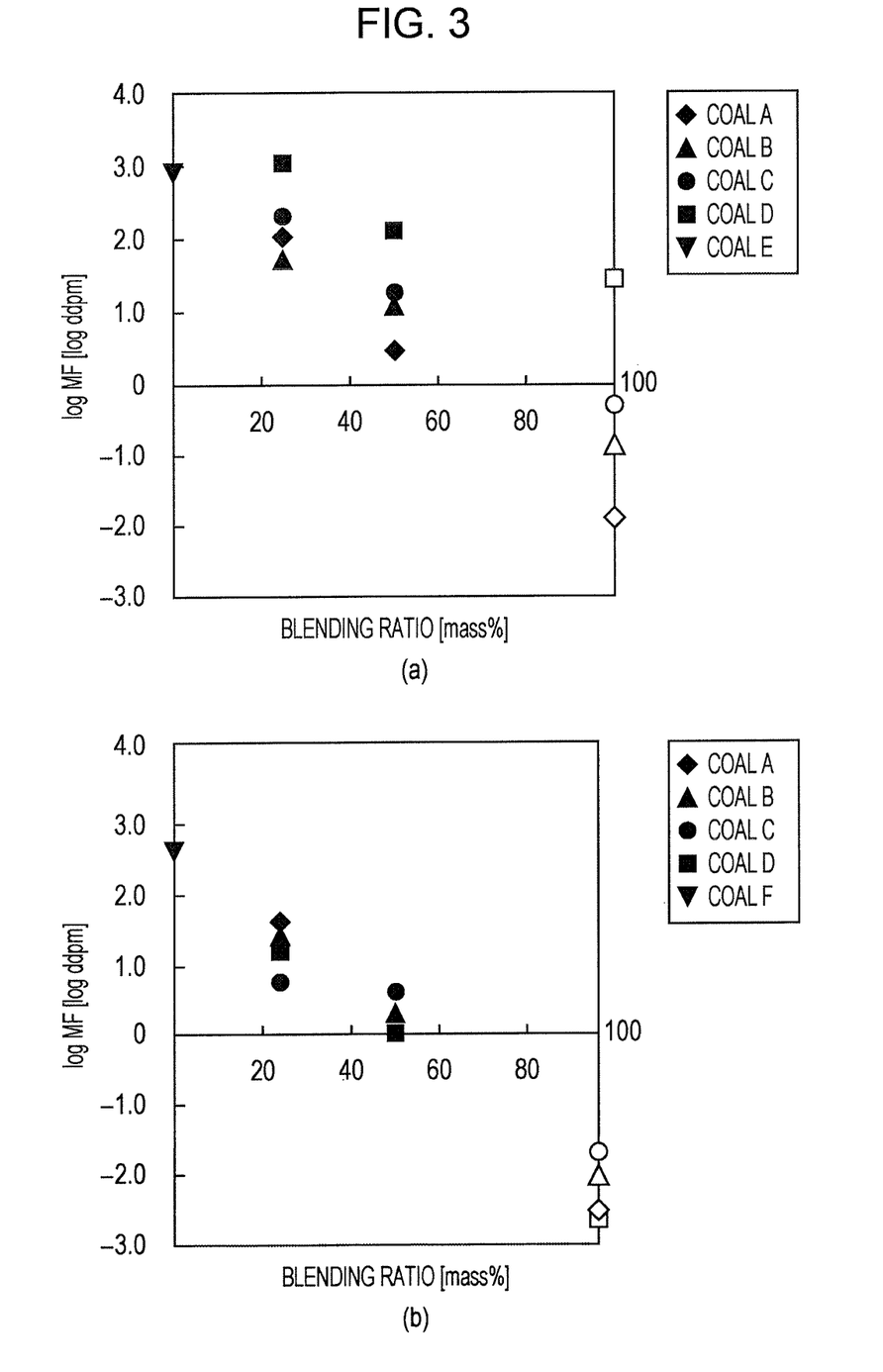
FIG. 3 includes graphs each illustrating the relationship between the blending ratio [mass %] of each of the evaluated coals in a coal blend and the log MF of the coal blend.

Coal blends were prepared such that Coals A to D:balance coals E and F=25%:75% by mass. The Gieseler maximum fluidity MF of each of the coal blends was measured. Coal blends were prepared such that Coals A to D:balance coals E and F=50%:50% by mass. The Gieseler maximum fluidity MF of each of the coal blends was measured. When the blending ratio of Coals A to D is 0% by mass, the coal blend is composed of only Coal E or F. In such a case, the common logarithm log MF of the Gieseler maximum fluidity MF of the coal blend may be determined from the MF value described in Table 3. FIG. 3 illustrates the relationship between the blending ratio [mass %] of each of Coals A to D in the coal blend and log MF [log ddpm] of the coal blend. In FIG. 3, FIG. 3(a) illustrates the relationship between the blending ratio of each of Coals A to D in a coal blend that included Coal E as a balance coal and the Gieseler maximum fluidity MF of the coal blend; and FIG. 3(b) illustrates the relationship between the blending ratio of each of Coals A to D in a coal blend that included Coal F as a balance coal and the Gieseler maximum fluidity MF of the coal blend.

The hollow dots shown in the graphs of FIGS. 3(a) and 3(b) are determined by plotting data obtained by the extrapolation of the sets of data on the blending ratios of Coals A to D that are 0%, 25%, and 50% by mass for each and the corresponding log MF values of Coals A to D. Since the coal blends having a blending ratio of 100% by mass is each composed of only a specific one of Coals A to D, the log MF values of the hollow dots are considered to be the log MF (estimated log MF) values of Coals A to D.

Figure 4:
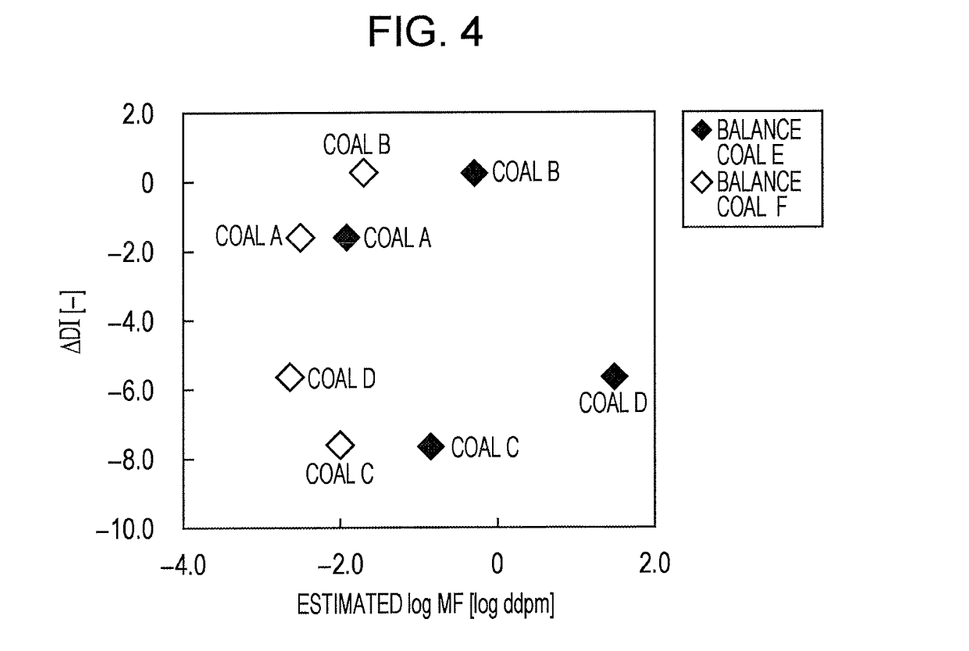
FIG. 4 is a graph illustrating the relationship between the log MF (estimated log MF) values of the evaluated coals which were determined on the basis of the graphs included in FIG. 3 and the $\Delta DI$ values.

FIG. 4 illustrates the relationship between the estimated log MF values of Coals A to D and the differences ΔDI. The graph of FIG. 4 does not confirm a correlation between the estimated log MF and the coke strength. This proves that it is even difficult to evaluate the impact of the type (Coals A to D) of a non- or slightly caking coal on the coke strength by estimating the Gieseler maximum fluidity of the non- or slightly caking coal by applying the contents of Patent Literature 3.

To Coals A to D, 10% by mass of a caking additive (asphalt pitch or coal-tar pitch), which has been known as being capable of enhancing the caking property of a coal, was added. Subsequently, the maximum fluidity MF of each of Coals A to D was measured. As in the preparation of the graph of FIG. 1, the relationship between the log MF values of coals including the caking additive and the ΔDI values was determined.

Figure 5:
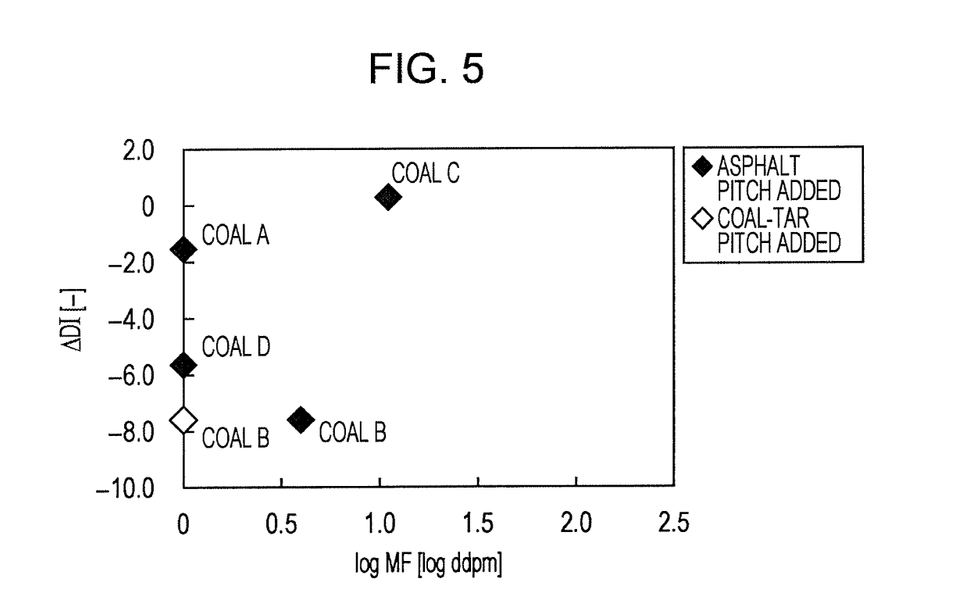
FIG. 5 is a graph illustrating the relationship between the log MF values of the evaluated coals which were measured after a pitch had been added to the coals and the $\Delta DI$ values.

FIG. 5 illustrates the relationship between log MF and ΔDI. When the maximum fluidity MF values of Coals A to D to which the caking additive had been added were 0 ddpm, the log MF values of the coals are denoted as 0 in the graph of FIG. 5. Some of the plotted dots overlap one another, since the MF values concerning each of Coals A, C, and D which were measured after the two types of caking additives had been added to the coal were equal to each other. The graph of FIG. 5 also does not confirm a correlation between the log MF values and ΔDI values. This proves that it is even difficult to evaluate the impact of the type of a non- or slightly caking coal (Coals A to D) on the coke strength when a caking additive is added to the non- or slightly caking coal in order to enhance the thermoplasticity of the non- or slightly caking coal.

As described above, it has been difficult in the related art to evaluate the impact of a non- or slightly caking coal on the coke strength. The inventors of the present invention conducted studies in order to enable the evaluation and, as a result, confirmed that a method for reforming a coal in which a primary or secondary amine including an aromatic ring is added to the coal in order to enhance the fluidity of the coal is described in Patent Literature 4. The inventors of the present invention extensively studied the feasibility of using the above amine for the above-described evaluation and, as a result, found that a physical property value relating to thermoplasticity of a non- or slightly caking coal that includes a primary or secondary amine including an aromatic ring has a positive correlation to the coke strength. Thus, the present invention was made.

Specifically, in embodiments of the present invention, a primary or secondary amine including an aromatic ring is added to a non- or slightly caking coal that is to be evaluated in order to enhance the thermoplasticity of the non- or slightly caking coal, and the non- or slightly caking coal is evaluated by using, as a measure, a physical property value of the non- or slightly caking coal which relates to the enhanced thermoplasticity of the coal.

The primary or secondary amine including an aromatic ring is preferably N,N'-di-2-naphthyl-p-phenylenediamine. The amine may also be a compound other than N,N'-di-2-naphthyl-p-phenylenediamine which is capable of enhancing the thermoplasticity (fluidity) of a coal when added to the coal. Specific examples of such a compound include phenothiazine, carbazole, and N-phenyl-1-naphthylamine, which are described in Patent Literature 4 as examples.

The inventors of the present invention further studied amines capable of markedly enhancing the MF of a coal and the regularity and, as a result, found that an amine having a high boiling point enhances the thermoplasticity of a coal when added to the coal. It is considered that, the higher the boiling point of an amine, the larger the amount of amine that remains in the temperature range of 350° C. to 550° C., in which the thermoplasticity of the coal occurs, and the higher the accuracy of representing the thermoplasticity of the coal. Among the above amines, N,N'-di-2-naphthyl-p-phenylenediamine has a high boiling point.

A test conducted for determining whether a physical property value relating to thermoplasticity of a non- or slightly caking coal including the amine has a positive correlation to the strength of a coke prepared from a coal blend including the non- or slightly caking coal is described. A physical property value relating to thermoplasticity used in the test was Gieseler maximum fluidity MF measured by a Gieseler plastometer method defined in JIS M 8801. The amine used in the test was N,N'-di-2-naphthyl-p-phenylenediamine described above.

The amine was added to each of Coals A to D in an amount corresponding to 5% or 10% by mass of the amount of coal in place of 5% or 10% by mass of the amount of coal, and the Gieseler maximum fluidity MF of the coal was measured. Table 4 shows the Gieseler maximum fluidity MF values measured.

TABLE 4

| Item | MF when 5 mass % of amine was added | MF when 10 mass % of amine was added |
|---|---|---|
| Unit | ddpm | |
| Coal A (semianthracite) | 1 | 17 |
| Coal B (subbituminous coal) | 0 | 0 |
| Coal C (subbituminous coal) | 8 | 86 |
| Coal D (anthracite) | 0 | 4 |

The MF values shown in Table 4 confirm that adding 10% by mass of the amine to a non- or slightly caking coal whose MF is not possible to be measured when the amine is not added to the coal enhances the thermoplasticity of the coal and makes it possible to measure the MF of the coal. On the other hand, adding 5% by mass of the amine to a non- or slightly caking coal enhances the thermoplasticity of the coal to some extent but may fail to markedly enhance the thermoplasticity of the coal depending on the brand of the coal. In such a case, the MF of the coal may fail to be measured.

Plural coals were mixed together to form a coal (balance coal) having a weighted mean Ro of 1.03 and a weighted mean log MF of 2.3. The balance coal was mixed with each of Coals A to D such that the blending ratio of Coals A to D was 20% by mass. Hereby, four types of coal blends were prepared. As in the preparation of the graph of FIG. 1, a coke was prepared from each of the four coal blends, and the drum strength of the coke was measured. Another coke was prepared by the carbonization of only the balance coal, the drum strength thereof was measured, and ΔDI was determined. The above coal blends did not include N,N'-di-2-naphthyl-p-phenylenediamine, which is capable of enhancing the thermoplasticity of a coal.

Figure 6:
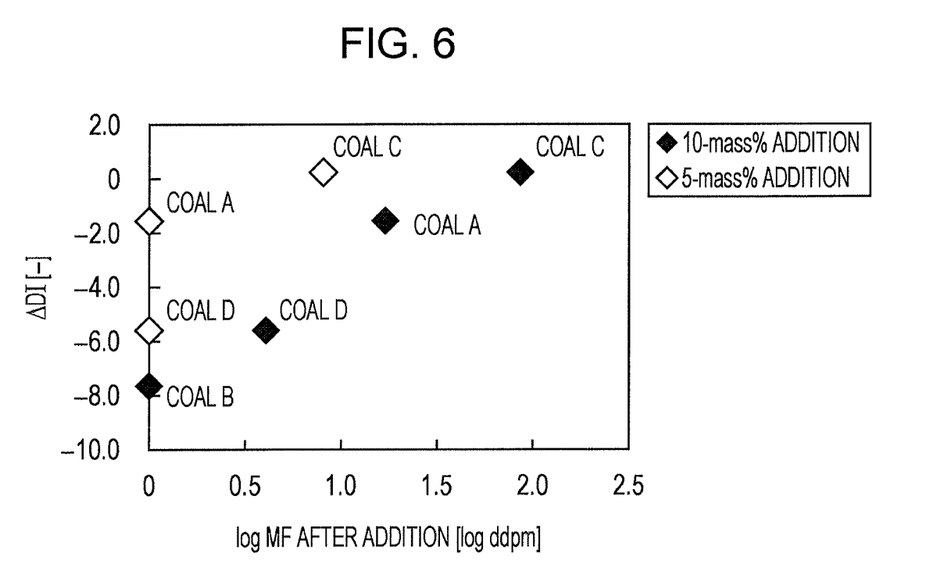
FIG. 6 is a graph illustrating the relationship between the log MF values of the evaluated coals which were measured after an amine had been added to the coals and the $\Delta DI$ values.

FIG. 6 illustrates the relationship between the log MF values of coals which were measured when 5% or 10% by mass of N,N'-di-2-naphthyl-p-phenylenediamine was added to the coals and corresponding ΔDI values. In FIG. 6, the plotted dots corresponding to Coal B overlap each other, because the log MF of Coal B was 0 in either case where the amount of N,N'-di-2-naphthyl-p-phenylenediamine added to Coal B was 5% or 10% by mass. The graph of FIG. 6 confirms that, the larger the log MF of a coal which was measured after 10% by mass of N,N'-di-2-naphthyl-p-phenylenediamine had been added to the coal, the smaller the amount of reductions in the ΔDI values in the case of Coals A, B, and D. It is also confirmed that the ΔDI values in the case of Coal C is positive.

Thus, the graph of FIG. 6 confirms a positive correlation between the Gieseler maximum fluidity of a non- or slightly caking coal which is measured after the amine has been added to the coal and the strength of a coke prepared from a coal blend that includes the coal. The positive correlation therebetween indicates the possibility of determining the usability of a non- or slightly caking coal, whose value on thermoplastic property is difficult (or, impossible) to measure, as a raw material for coke on the basis of the fluidity of the coal which is measured after a primary or secondary amine including an aromatic ring has been added to the coal.

The inventors of the present invention conducted an additional test in which different types of non- or slightly caking coals were evaluated in order to verify the good positive correlation between the fluidity of a non- or slightly caking coal which is measured after a primary or secondary amine including an aromatic ring has been added to the coal and the strength of a coke prepared from a coal blend that includes the coal. Table 5 shows the evaluated non- or slightly caking coals. Coals G to I shown in Table 5 are slightly caking coals having a low Gieseler maximum fluidity MF.

TABLE 5

| Item<br>Unit | Ro<br>% | VM<br>% dry basis | MF<br>ddpm |
|---|---|---|---|
| Coal G (bituminous coal) | 1.000 | 26.6 | 20 |
| Coal H (bituminous coal) | 1.017 | 23.9 | 1 |
| Coal I (bituminous coal) | 0.794 | 33.6 | 3 |

In the additional test, the impact of each of the slightly caking coals (Coals G to I) on the coke strength which occurs when the slightly caking coal is included in a coal blend was determined using a carbonization test oven. In order to simulate an actual operation in which the average quality of a coal blend is adjusted to be a target quality, the composition and quality of the balance of each coal blend, which is a portion of the coal blend which is other than the non- or slightly caking coal to be evaluated, were adjusted such that the coal blend including a non- or slightly caking coal had the same average quality. Specifically, the adjustment of the balance coal was made such that the blending ratio of a non- or slightly caking coal in each coal blend was 0% or 15% by mass and the average qualities of the coal blend were an average Ro of 1.05 and an average common logarithm of MF (log MF) of 2.5. Thus, three coal blends including the respective three coals shown in Table 5 and one coal blend that does not include any of the coals shown in Table 5, that is, four coal blends in total, were prepared. The coal blends were each charged into a carbonization vessel such that the bulk density (in terms of dry weight) of the coal blend was 725 kg/m$^3$, at which a coal is charged from the upper portion of a coke oven chamber in a common operation. Carbonization was performed on each of the coal blends for 6 hours in an electric furnace having a furnace temperature of 1050° C. with a 10-kg weight being placed on the carbonization vessel. Subsequently, the carbonized coal blends were removed from the electric furnace and cooled with nitrogen. Hereby, coke was prepared. In accordance with the method for testing drum strength described in JIS K 2151, the coke was each rotated 150 times at a rotational speed of 15 rpm and the mass proportion of coke particles having a diameter of 15 mm or more was measured. The strength of the coke was evaluated in terms of drum strength index DI(150/15) [–], which is calculated by multiplying the mass ratio relative to the coke that has not been rotated by 100.

The usability of each of the non- or slightly caking coals as a raw material for coke was evaluated on the basis of the difference ΔDI calculated by subtracting, from the drum strength of a coke prepared from a coal blend that included a specific one of Coals G to I, the drum strength of a coke prepared from a coal blend that did not include any of Coals G to I. A negative ΔDI concerning a non- or slightly caking coal indicates that adding the coal to a coal blend reduced the strength of the resulting coke compared with a coke prepared from a coal blend that did not include any of Coals G to I.

Figure 7:
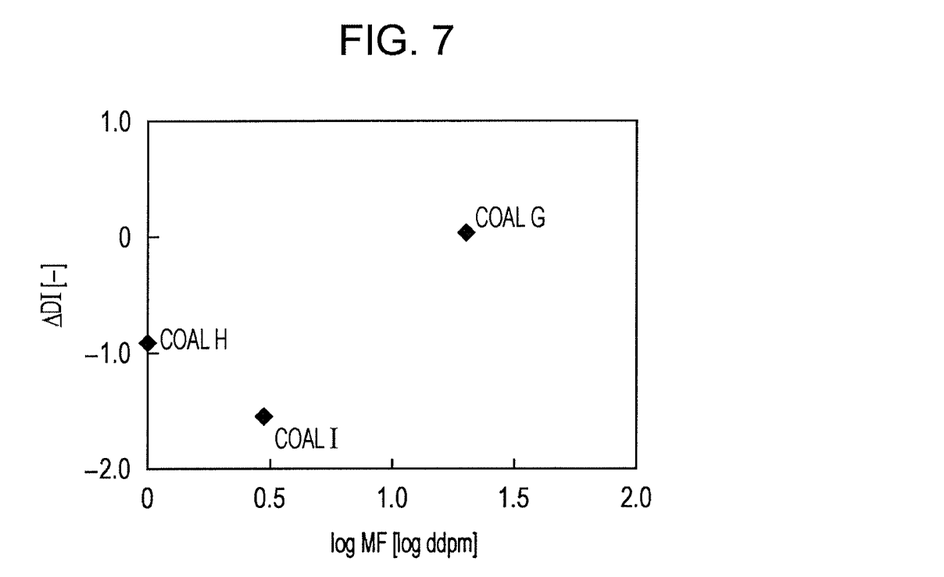
FIG. 7 is a graph illustrating the relationship between the log MF values of the evaluated coals which were included in the respective coal blends and the $\Delta DI$ values.

FIG. 7 illustrates the relationship between the log MF values of Coals G to I and corresponding ΔDI values. The graph of FIG. 7 shows that the strength of a coke prepared from a coal blend that included Coal H or I was smaller than the strength of a coke prepared from a coal blend that did not include Coal H or I. It is also confirmed that, as for the log MF values of the non- or slightly caking coals (Coals H and I), although Coal H had a smaller log MF value, the amount of reduction (ΔDI of FIG. 7) in the strength of a coke prepared from a coal blend that included Coal H compared with the strength of a coke prepared from a coal blend that did not include the non- or slightly caking coal is smaller than the amount of reduction in the strength of a coke prepared from a coal blend that included Coal I. This also confirms the difficulty in accurately evaluating the impacts of the type of a non- or slightly caking coal on the coke strength by only measuring a physical property value (Gieseler maximum fluidity) of the non- or slightly caking coal which relates to thermoplasticity.

N,N'-di-2-naphthyl-p-phenylenediamine, which served as an amine, was added to each of Coals G to I in an amount corresponding to 10% by mass of the amount of coal in place of 10% by mass of the amount of coal. Subsequently, the Gieseler maximum fluidity MF of each of Coals G to I containing the amine was measured. Table 6 shows the results of the measurement of Gieseler maximum fluidity MF.

TABLE 6

| Item<br>Unit | MF when 10 mass % of amine was added<br>ddpm |
|---|---|
| Coal G (bituminous coal) | 31396 |
| Coal H (bituminous coal) | 6167 |
| Coal I (bituminous coal) | 588 |

The MF values shown in Table 6 confirm that adding 10% by mass of the amine to the coals increased the MF values of the coals compared with the MF values of the coals that did not include the amine, that is, adding the amine to the coals enhanced the thermoplasticity of the coals. It is also confirmed that the order of log MF values of the coals described in Table 6, which were measured after the amine had been added to the coals, is different from the order of log MF values of the coals described in Table 5.

Figure 8:
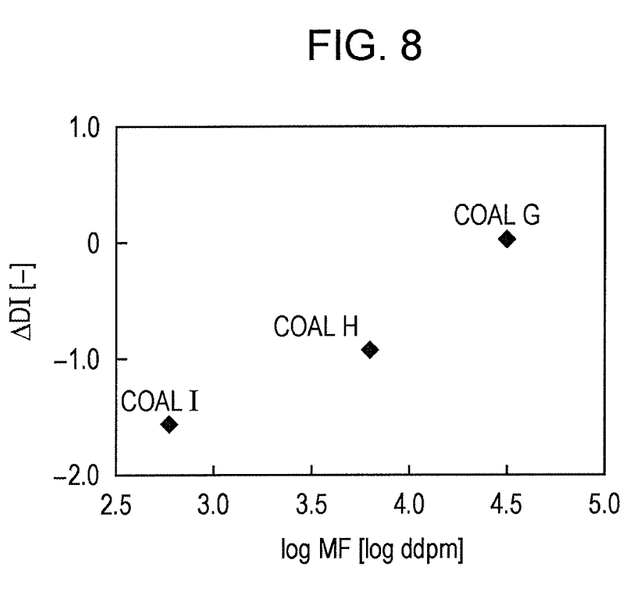
FIG. 8 is, a graph illustrating the relationship between the log MF values of the evaluated coals which were measured after an amine had been added to the coals and the $\Delta DI$ values.

FIG. 8 illustrates the relationship between the log MF values of the coals which were measured after 10% by mass of N,N'-di-2-naphthyl-p-phenylenediamine had been added to the coals and corresponding ΔDI values. The graph of FIG. 8 confirms that, the larger the log MF of a coal which was measured after 10% by mass of N,N'-di-2-naphthyl-p-phenylenediamine had been added to the coal, the smaller the amount of reduction in ΔDI.

The results of the test in which the graph of FIG. 6 was obtained and the results of the above additional test confirm that there was a positive correlation between the Gieseler maximum fluidity of a slightly caking coal which was measured after the amine had been added to the coal and the strength of a coke prepared from a coal blend that included the coal even when the type of the coal and the bulk density of the coal in the production of the coke were changed. Accordingly, it became evident that it is possible to accurately determine the usability of a non- or slightly caking coal, whose value on thermoplastic property is difficult (or, impossible) to measure otherwise, as a raw material for coke on the basis of the fluidity of the coal which is measured after a primary or secondary amine including an aromatic ring has been added to the coal.

Although it is described in Patent Literature 4 that adding a primary or secondary amine including an aromatic ring to a coal enhances the fluidity of the coal, it is not known that the suitability of a coal as a raw material for coke can be evaluated on the basis of the fluidity of the coal which is measured after a primary or secondary amine including an aromatic ring has been added to the coal. The method according to embodiments of the present invention makes it possible to evaluate the suitability of a coal which has been impossible to evaluate in the related art and to clearly determine whether or not the coal is usable as a raw material for coke.

The usability of the evaluated coal as a raw material for coke may be determined in the following manner. In the case where plural sets of data on the physical property value (Gieseler maximum fluidity) relating to thermoplasticity of each of plural brands of coals and the strength of a coke prepared from a coal blend including the coal are available and there is a positive correlation between the physical property values relating to thermoplasticity of the coals and the plurality of strength of the coke as in FIGS. 6 and 8, the usability of a coal (in particular, a non- or slightly caking coal) as a raw material for coke can be determined in the following manner.

[I] A relational formula between the physical property value relating to thermoplasticity of a coal and the coke strength can be determined from the plural sets of data. The relational formula may be determined by, for example, drawing a calibration curve by the method of least squares or freehand on the graph of FIG. 6 or 8.

[II] A physical property value of a coal which corresponds to the target coke strength (ΔDI) is determined using the relational formula derived in [I] above. The target coke strength is the strength of a coke that can be used in the operation of a blast furnace and can be determined in advance. For example, the difference (e.g., ΔDI) between the strength of a coke prepared from a coal blend including a non- or slightly caking coal and the strength of a coke prepared from the balance of the coal blend can be estimated on the basis of the sets of data obtained by a carbonization test. When the strength of a coke prepared from the balance of the coal blend to which a non- or slightly caking coal has not yet been added is known, it is possible to determine the strength of a coke prepared from a coal blend to which the non- or slightly caking coal has been added by adding the estimated ΔDI to the strength of a coke prepared from the balance of the coal blend. When the strength of a coke prepared from the coal blend including the non- or slightly caking coal, which is determined in the above-described manner, is larger than the strength required for coke, the non- or slightly caking coal is evaluated as being usable as a raw material for coke. This also makes it possible to determine the physical property value relating to thermoplasticity of a non- or slightly caking coal at which the strength of a coke prepared from a coal blend including the non- or slightly caking coal is equal to the strength required for coke.

[III] The physical property value relating to thermoplasticity of a coal that is to be measured is measured. When the physical property value of the coal is larger than the specific physical property value determined above, a coke prepared from a coal blend including the coal is considered to have a suitable coke strength. In particular, when a coal that is to be measured is added to a balance coal in order to prepare a coal blend at the blending ratio at which each of the coals was included in a coal blend when the above-described sets of data were obtained in [I], a coke prepared from the coal blend is expected to have a coke strength larger than the predetermined target strength.

However, as shown by the dots included in the graph of FIG. 6 which correspond to the results obtained when the amount of amine added was 5% by mass, if the amount of amine added is excessively small, the thermoplasticity of a non- or slightly caking coal may fail to be enhanced to a sufficient level and, as a result, the accuracy of the evaluation of the thermoplasticity of the coal may be degraded. Thus, it is considered that there is a suitable ratio at which the amine is added to a non- or slightly caking coal in order to enhance the thermoplasticity of the coal, depending on the types of amine and non- or slightly caking coal used. Accordingly, the inventors of the present invention studied a method for determining an amount of amine which is optimum for enhancing the thermoplasticity of a non- or slightly caking coal, which varies with the type of amine and the brand of non- or slightly caking coal.

The type and amount of amine added to a non- or slightly caking coal are determined in the following manner.

[1] An amine capable of enhancing the fluidity of a coal when added to the coal is selected as an amine that is to be used.

[2] The selected amine is added to plural types of coals (preferably, noncaking coals having an MF of 0) that are to be evaluated in a predetermined amount. The MF values of the coals are subsequently measured.

[3A] When the MF values of the coals that are to be evaluated differ from one another, it is considered that the amount of amine and the type of amine selected are determined as being usable for evaluation.

[3B] When the MF values of the coals that are to be evaluated do not differ from one another, the amount of amine is increased or another amine having a higher boiling point than the amine selected in [1] is added to the coals. Subsequently, the measurement described in [2] is again conducted.

After the type of the amine and the adequate amount of amine which corresponds to the type of amine have been determined, the specific amount of amine is added to a non- or slightly caking coal, a physical property value of the coal which relates to thermoplasticity is measured, and the usability of the coal as a raw material for coke may be evaluated by using the measured physical property value as a measure. When the physical property values of coals which relate to thermoplasticity are measured under the same amine-addition conditions and the correlation between the measured physical property values of the coals and the plurality of strength of coke prepared by the carbonization of coal blends including the coals is determined in advance, it becomes possible to determine the usability of a coal whose usability as a raw material for coke is unknown as a raw material for coke on the basis of the physical property value of the coal relating to thermoplasticity which is measured in easier manner by adding an amine to the coal without conducting a carbonization test, which requires effort and time. The carbonization of a coal blend including a coal evaluated as being usable enables a coke capable of maintaining a high strength to be produced.

The coal to which the amine is added is preferably a non- or slightly caking coal having a Gieseler maximum fluidity MF of 20 ddpm or less. In general, coals having a Gieseler maximum fluidity MF of 0 ddpm are referred to as noncaking coals, and coals having a Gieseler maximum fluidity MF of about 100 ddpm or less are referred to as slightly caking coals. Since Gieseler maximum fluidity measured by the JIS method is an integer, the accuracy of measurement is low when MF is 10 ddpm or less. Therefore, applying the method according to the present invention to a coal having an MF of 10 ddpm or less is particularly advantageous. It is not possible to determine the difference in thermoplasticity between coals that are noncaking coals having an MF of 0. The advantageous effects of the present invention, which make it possible to evaluate the difference in thermoplasticity between coals, which affects the coking properties of coals, on the basis of measurement of the MF values of the coals to which an amine has been added, become remarkable when non- or slightly caking coals having a negligible or considerably small Gieseler maximum fluidity MF are used. Thus, the target to be evaluated in the present invention is a coal having a relatively small Gieseler maximum fluidity MF (MF 20 ddpm) whose thermoplasticity can be markedly enhanced when an amine is added to the coal.

Although the physical property value relating to thermoplasticity used in the above-described embodiment is Gieseler maximum fluidity MF, the physical property value relating to thermoplasticity used in the present invention is not limited to Gieseler maximum fluidity MF. Examples of the thermoplastic physical properties include the dilatability, adhesiveness, permeability, and viscosity of a melted coal. Specific examples of the physical property values include total dilatation measured with a dilatometer, specific dilatation volume, permeation distance, and viscoelasticity.

Although the physical property values of plural brands of coals which relate to thermoplasticity and a plurality of the coke strength are directly measured respectively in the above-described embodiment, they are not necessarily measured directly in the present invention. When the sets of data on the physical property values of coals which relate to thermoplasticity and the plurality of coke strength are available and provided by a third party, it is possible to determine a relational formula between the physical property values of coals and the plurality of coke strength and evaluate the usability of a coal as a raw material for coke.

As described above, the evaluating method according to the present invention makes it possible to evaluate the impact of a non- or slightly caking coal on the strength of a coke prepared from a coal blend including the non- or slightly caking coal. This makes it possible to determine a coal (non- or slightly caking coal) for a coal blend that is capable of maintaining high coke strength.

The invention claimed is:

1. An evaluating method for a coal for use as a raw material for coke, the method comprising:
   adding a primary or secondary amine comprising an aromatic ring to modify the coal to be evaluated, the coal having a Gieseler maximum fluidity MF of 20 ddpm or less before the amine is added to the coal; and
   evaluating the coal to determine whether the coal is usable for the raw material for coke, the coal being usable if a Gieseler maximum fluidity MF of the modified coal is greater than the Gieseler maximum fluidity MF of the coal to which the primary or secondary amine including an aromatic ring is not added.

2. The evaluating method according to claim 1, wherein the amine is N,N'-di-2-naphthyl-p-phenylenediamine.

3. A producing method for a coke, the producing method comprising:
   evaluating a coal as being usable to produce a coke using the evaluating method according to claim 2; and
   carbonizing a coal blend including the coal evaluated as being usable to produce a coke.

4. A producing method for a coke, the producing method comprising:
   evaluating a coal as being usable to produce a coke using the evaluating method according to claim 1; and
   carbonizing a coal blend including the coal evaluated as being usable to produce a coke.

5. An evaluating method for a coal which has a Gieseler maximum fluidity MF of 20 ddpm or less and which is used as a raw material for coke, the method comprising:
   selecting a plurality of coals to be subjected to carbonization tests, the coals having a Gieseler maximum fluidity MF of 20 ddpm or less;
   adding a primary or secondary amine comprising an aromatic ring to modify the plurality of coals;
   obtaining a plurality of Gieseler maximum fluidity MF values of mixtures including each of the selected plurality of coals modified with addition of a primary or secondary amine including an aromatic ring, as well as a plurality of coke strengths of each of the plurality of cokes produced by carbonization of a coal blend including each coal of the selected plurality of coals without addition of the primary or secondary amine;
   determining a Gieseler maximum fluidity MF value corresponding to a target value of coke strength from a relational formula between the obtained Gieseler maximum fluidity MF values and the plurality of the coke strengths corresponding to each of the obtained Gieseler maximum fluidity MF values; and evaluating a coal, without the addition of the primary or secondary amine, to determine whether the coal is usable for a raw material for coke, the coal being usable if a Gieseler maximum fluidity MF value of the coal obtained with addition of the primary or secondary amine including an aromatic ring is equal to or larger than the determined Gieseler maximum fluidity MF value.

6. A producing method for a coke, the producing method comprising:

evaluating a coal as being usable to produce a coke using the evaluating method according to claim 5; and carbonizing a coal blend including the coal evaluated as being usable to produce a coke.

7. The evaluating method according to claim 5, wherein the amine is N,N'-di-2-naphthyl-p-phenylenediamine.

8. A producing method for a coke, the producing method comprising:

evaluating a coal as being usable to produce a coke using the evaluating method according to claim 7; and carbonizing a coal blend including the coal evaluated as being usable to produce a coke.

* * * * *